United States Patent [19]

Kubo et al.

[11] Patent Number: 6,063,831

[45] Date of Patent: May 16, 2000

[54] METHOD FOR PROCESSING DENTAL ACRYLIC RESINS

[75] Inventors: Fuminobu Kubo, Katano; Kazuhiko Joshin, Yokosuka, both of Japan

[73] Assignee: GC Corporation, Tokyo, Japan

[21] Appl. No.: 09/182,009

[22] Filed: Oct. 29, 1998

[30] Foreign Application Priority Data

Nov. 7, 1997 [JP] Japan .................................. 9-322475

[51] Int. Cl.[7] ....................................................... A61F 2/00
[52] U.S. Cl. ................................................................. 523/115
[58] Field of Search ................................................ 523/115

[56] References Cited

U.S. PATENT DOCUMENTS

| | | | |
|---|---|---|---|
| 3,836,153 | 9/1974 | Dance | 273/173 |
| 4,001,939 | 1/1977 | Gross | 32/15 |
| 4,268,639 | 5/1981 | Seidel | 525/303 |
| 4,361,528 | 11/1982 | Ginsberg | 264/28 |
| 4,670,208 | 6/1987 | Koblischek | 264/250 |
| 5,869,557 | 2/1999 | Landru | 524/399 |

*Primary Examiner*—Paul R. Michl
*Attorney, Agent, or Firm*—Oblon, Spivak, McClelland, Maier Neustadt, P.C.

[57] ABSTRACT

A method for using dental acrylic resins, the method comprising mixing a liquid monomer of methyl methacrylate with a polymer powder of methyl methacrylate, forming the mixture into an arbitrary shape by molding, filling, applying or other means, and then polymerizing and curing the formed mixture, wherein organic compounds selected from acryloyl morpholine, a coumarone resin, vinyl stearate, polyvinyl acetate, and alcoholic surfactants are previously added to the liquid monomer as a shrinkage controlling agent for lowering a curing shrinkage caused by the polymerization, is disclosed. According to the invention, not only the curing shrinkage rate of the curing shrinkage generated at the time of polymerization can be readily lowered to 0.3% or less, but also the method of the invention can be applied to a denture, a denture base, a casting pattern, fillers or cements as in the conventional techniques.

11 Claims, No Drawings

METHOD FOR PROCESSING DENTAL ACRYLIC RESINS

FIELD OF THE INVENTION

The present invention relates to a method for using dental acrylic resins, which enables to make small the curing shrinkage generated at the time of polymerization.

BACKGROUND OF THE INVENTION

As a method for using acrylic resins in dental applications, there is known a method in which a polymer powder of methyl methacrylate and a liquid monomer of methyl methacrylate are mixed with each other in a weight ratio of about 2/1, the mixture is allowed to stand for 10 minutes or longer to be a dough, and the dough is then filled in a mold or gypsum mold for molding a denture or denture base, or cavities of teeth, thereby allowing it to polymerize and cure. And as a polymerization means, there is known a heat polymerization method in which the above-described polymer powder is previously added with benzoyl peroxide as a polymerization initiator, and after filling the dough in the mold, it is heated at 60° C. or higher, thereby decomposing the benzoyl peroxide to start the polymerization. Since in this method, moldings with a high strength can be obtained, this method is employed for molding a denture and the like.

In addition, there are also known a low temperature polymerization method in which while adding benzoy peroxide to the polymer powder, the liquid monomer is added by a tertiary amine, and the tertiary amine is brought into contact with benzoyl peroxide upon mixing of the liquid monomer with the polymer powder, thereby decomposing the benzoyl peroxide to start the polymerization; a photo-polymerization method in which a photo-sensitizer is used in place of the tertiary amine in the above-described autopolymerization method, the photo-sensitizer is decomposed upon irradiation with ultraviolet rays or visible rays, thereby decomposing the benzoyl peroxide with the decomposition product to start the polymerization; and the like. Since these methods do not need heating, they are employed for applications of fillers or cements for filling in or applying on cavities of teeth and the like. In the foregoing low temperature polymerization method or photopolymerization method, by attaching the polymer powder to a brush tip soaking up the liquid monomer, the mixing of the liquid monomer with the polymer powder is carried out, and a spherical viscous mixture at the brush tip is filled in or applied on cavities of teeth, thereby molding it in an arbitrary shape.

However, in the above-described method, even when any of the heat polymerization method, low temperature polymerization method, or photopolymerization method is employed for the polymerization, the curing shrinkage caused by the polymerization of the monomer is as high as about 0.5 to 0.6% in terms of the curing shrinkage rate. For example, in case that a denture base is prepared, there was an inconvenience that a space is formed in the back surface (mucous membrane) side, resulting in poor fitness. And an attempt in which the polymerization is carried out from the back surface side to prevent the shrinkage in the back surface side, thereby preventing the poor fitness of the denture base is being made. In this case, however, there was still a problem that since shrinkage occurs in the front surface side opposite to the back surface side, the biting becomes worse.

SUMMARY OF THE INVENTION

An object of the present invention is to provide a method for using dental acrylic resins, which enables to make small the curing shrinkage generated at the time of polymerization. That is, in the present invention, in a method using a polymer powder of methyl methacrylate and a liquid monomer of methyl methacrylate, specific additives are added, thereby modifying a dental acrylic resin itself so that the curing shrinkage, the occurrence of which has hitherto been considered to be inevitable, is lowered to 0.3% or less in terms of the curing shrinkage rate. Also, like in the conventional techniques, the present invention can be employed not only for molding a denture, denture base or casting pattern but also for filling in or applying on cavities of teeth.

The object of the present invention can be achieved by a method for using dental acrylic resins, the method comprising mixing a liquid monomer of methyl methacrylate with a polymer powder of methyl methacrylate, forming the mixture into an arbitrary shape by molding, filling, applying or other means, and then polymerizing and curing the formed mixture, wherein organic compounds selected from acryloyl morpholine, coumarone resin, vinyl stearate, polyvinyl acetate, and alcoholic surfactants are previously added to the liquid monomer as a shrinkage controlling agent for lowering the curing shrinkage caused by the polymerization.

In the method of the present invention, like in the conventional techniques, in order to make the polymerization of the liquid monomer possible, not only benzoyl peroxide is previously added to the polymer powder, but also a tertiary amine or a photo-sensitizer is previously added to the liquid monomer depending upon the polymerization method employed.

DETAILED DESCRIPTION OF THE INVENTION

As the shrinkage controlling agent, any materials which can lower the curing shrinkage rate at the time of polymerization to 0.3% or less without impairing mechanical properties or appearance of polymerized articles can be employed. Examples of such shrinkage controlling agent include acryloyl morpholine, coumarone resin, vinyl stearate, polyvinyl acetate, and alcoholic surfactants. They can be use singly or in admixture of two or more thereof. In case of a single use, the curing shrinkage rate can be lowered to about 0.2% depending on an addition amount selected. In case of mixing, preferred organic compounds are a mixture of at least one of acryloyl morpholine, coumarone resin, and polyvinyl acetate with an alcoholic surfactant, and the curing shrinkage rate can be lowered to about 0.1%.

The acryloyl morpholine is a colorless, transparent liquid water-soluble monomer represented by a chemical formula, $C_7H_{11}NO_2$ and is preferably added in an amount of from 5 to 15% based on the weight of the liquid monomer of methyl methacrylate. The addition of the acryloyl morpholine can achieve the curing shrinkage rate of from 0.2 to 0.3%. If the amount of the acryloyl morpholine to be added is less than 5% by weight, no effect can be obtained, whereas the addition amount exceeding 15% by weight is not economical.

The coumarone resin is a copolymer of coumarone, indene and styrene and preferably added in an amount of from 0.5 to 10% based on the weight of the liquid monomer of methyl methacrylate. The addition of the coumarone resin can achieve the curing shrinkage rate of from 0.2 to 0.3%. If the amount of the coumarone resin to be added is less than 0.5% by weight, no effect can be obtained, whereas if the addition amount exceeds 10% by weight, the tackiness increases, whereby the resulting mixture is difficult to be handled.

A preferred amount of the vinyl stearate which is added is from 5 to 15% based on the weight of the liquid monomer of methyl methacrylate, and at this time, the curing shrinkage rate becomes from 0.2 to 0.3%. If the addition amount is less than 5% by weight, no effect can be obtained, whereas if the addition amount exceeds 15% by weight, the surface of a polymerized article becomes rough, such is not preferred.

A preferred amount of the polyvinyl acetate which is added is from 0.5 to 10% based on the weight of the liquid monomer of methyl methacrylate, and at this time, the curing shrinkage rate becomes from 0.2 to 0.3%. If the addition amount is less than 0.5% by weight, no effect can be obtained, whereas if the addition amount exceeds 10% by weight, the tackiness increases, whereby the resulting mixture is difficult to be handled.

As the alcoholic surfactant, any materials which are soluble in the above-described liquid monomer can be used. In particular, those having a higher number of carbon atoms are preferred, and specific examples thereof include stearyl alcohol (including isomers), oleyl alcohol, pentadecyl alcohol, and pentaerythritol. A preferred amount of the alcoholic surfactant which is added is from 0.1 to 5.0% based on the weight of the liquid monomer of methyl methacrylate, and at this time, the curing shrinkage rate becomes from 0.2 to 0.3%. If the addition amount is less than 0.1% by weight, no effect can be obtained, whereas if the addition amount exceeds 5.0% by weight, the surface of the polymerized article becomes rough, and its strength is lowered.

In case that any two or more of the above-described acryloyl morpholine, coumarone resin, vinyl stearate, polyvinyl acetate and alcoholic surfactant are mixed, their addition amount is appropriately set up depending upon a combination of the organic compounds to be used. For example, in case that any one of acryloyl morpholine or vinyl stearate is mixed with either one of the coumarone resin or polyvinyl acetate, it is preferred that a total addition amount is from 0.5 to 15% by weight, with an addition amount of either one of the coumarone resin or polyvinyl acetate being from 0.5 to 10% by weight. Further, in case that any one of acryloyl morpholine or vinyl stearate is mixed with the alcoholic surfactant, it is preferred that a total addition amount is set from 0.1 to 15% by weight, with an addition amount of the alcoholic surfactant being from 0.1 to 5% by weight. Still further, in case that the coumarone resin or polyvinyl acetate is mixed with he alcoholic surfactant, it is preferred that a total addition amount is set from 0.1 to 10% by weight, with an addition amount of the alcoholic surfactant being from 0.1 to 5% by weight.

In particular, in case that any one or more of the acryloyl morpholine, coumarone resin and polyvinyl acetate are mixed with the alcoholic surfactant such as stearyl alcohol, it is possible to further decrease the curing shrinkage rate to 0.13% or less. And in case that three members of acryloyl morpholine, coumarone resin and isostearyl alcohol are mixed (coumarone resin can be substituted with polyvinyl acetate), with addition amounts of the respective organic compounds being set up at 10%, 1.0% and 0.5%, respectively based on the weight of the liquid monomer, not only the curing shrinkage rate is a minimum value of 0.1%, but also the surface of a polymerized article is smooth. In mixing the above-described three members, in case that a coumarone resin is used, since the coumarone resin is hydrophobic, the resulting mixture can be suitably used for molding a denture base, whereas in case that polyvinyl acetate is used, since the polyvinyl acetate is hydrophilic, the resulting mixture is suitably used as a casting pattern.

(Embodiment 1)

A polymer powder of methyl methacrylate and a liquid monomer of methyl methacrylate are mixed with each other in a weight ratio of about 2/1, and the mixture is allowed to stand for from 10 to 30 minutes to be a dough. In this case, the polymer powder is previously mixed with from 0.5 to 1.0% by weight of benzoyl peroxide according to a customary manner, while the liquid monomer is previously added with from 5 to 15% by weight of acryloyl morpholine. Then, the thus obtained dough is filled in an arbitrary mold or gypsum mold and heated at from 60 to 100° C. for 30 minutes thereby effecting polymerization of the dough. After cooling, a polymerized article is taken out of the mold or gypsum mold. Incidentally, the above-described acryloyl morpholine can be replaced by from 0.5 to 10% by weight of a coumarone resin, from 5 to 15% by weight of vinyl stearate, from 0.5 to 10% by weight of polyvinyl acetate, or from 0.1 to 5.0% by weight of an alcoholic surfactant.

(Embodiment 2)

The liquid monomer used in Embodiment 1 is added with from 0.5 to 3.0% by weight of a tertiary amine in addition to the above-described 5 to 15% by weight of acryloyl morpholine, and the resulting liquid monomer is soaked through a brush tip, to which the benzoyl peroxide-containing polymer powder is then attached. A spherical mixture at the brush tip is filled in cavities of teeth or the like, or applied on a desired portion, and then allowed to stand at room temperature for from 3 to 5 minutes thereby effecting polymerization and curing of the mixture. Incidentally, the above-described acryloyl morpholine can be replaced by from 0.5 to 10% by weight of a coumarone resin, from 5 to 15% by weight of vinyl stearate, from 0.5 to 10% by weight of polyvinyl acetate, or from 0.1 to 5.0% by weight of an alcoholic surfactant.

(Embodiment 3)

A spherical mixture at the brush tip is filled in or applied on a desired portion in the same manner as in Embodiment 2, except that a photo-sensitizer (camphorquinone (hereinafter abbreviated as (CQ)) is added in place of the tertiary amine as used in Embodiment 2. The mixture is then irradiated with ultraviolet rays or visible rays thereby effecting polymerization and curing of the mixture. Incidentally, the above-described acryloyl morpholine can be replaced by from 0.5 to 10% by weight of a coumarone resin, from 5 to 15% by weight of vinyl stearate, from 0.5 to 10% by weight of polyvinyl acetate, or from 0.1 to 5.0% by weight of an alcoholic surfactant.

(Embodiment 4)

A method for using dental acrylic resins in a heat polymerization is carried out in the same manner as in Embodiment 1, except that the liquid monomer is added with an alcoholic surfactant in addition to the acryloyl morpholine. In this case, a total addition amount of the acryloyl morpholine and the alcoholic surfactant is from 0.1 to 15% by weight, in which the addition amount of the alcoholic surfactant is from 0.1 to 5.0% by weight, with the remainder being of the acryloyl morpholine. The acryloyl morpholine can be replaced by a coumarone resin or polyvinyl acetate. In this case, a total addition amount of the coumarone resin or polyvinyl acetate and the alcoholic surfactant is from 0.1 to 10%, in which the addition amount of the alcoholic surfactant is from 0.1 to 2.0% by weight, with the remainder being of the coumarone resin or polyvinyl acetate.

(Embodiment 5)

A method for using dental acrylic resins in a low temperature polymerization is carried out in the same manner as in Embodiment 2, except that the liquid monomer is added with an alcoholic surfactant in addition to the acryloyl morpholine. In this case, the addition amounts of the acryloyl morpholine and the alcoholic surfactant are set up in the same manner as in Embodiment 4. The acryloyl morpholine can be replaced by a coumarone resin or polyvinyl acetate in a similar fashion to Embodiment 4.

(Embodiment 6)

A method for using dental acrylic resins in a photopolymerization is carried out in the same manner as in Embodiment 3, except that the liquid monomer is added with an alcoholic surfactant in addition to the acryloyl morpholine. In this case, the addition amounts of the acryloyl morpholine and the alcoholic surfactant are set up in the same manner as in Embodiments 4 and 5. The acryloyl morpholine can be replaced by a coumarone resin or polyvinyl acetate in a similar fashion to Embodiments 4 and 5.

(Embodiment 7)

A method for using dental acrylic resins in a heat polymerization is carried out in the same manner as in Embodiment 1, except that the liquid monomer is added with a coumarone resin and an alcoholic surfactant in addition to the acryloyl morpholine. In this case, a total addition amount of the acryloyl morpholine, the coumarone resin and the alcoholic surfactant is from 5 to 15% by weight, in which the addition amount of the alcoholic surfactant is from 0.1 to 2.0% by weight, and the addition amount of the coumarone resin is from 0.5 to 3.0% by weight, the remainder being of the acryloyl morpholine. The coumarone resin can be replaced by polyvinyl acetate.

(Embodiment 8)

A method for using dental acrylic resins in a low temperature polymerization is carried out in the same manner as in Embodiment 2, except that the liquid monomer is added with a coumarone resin and alcoholic surfactant in addition to the acryloyl morpholine. In this case, the addition amounts of the acryloyl morpholine, the coumarone resin and the alcoholic surfactant are set up in the same manner as in Embodiment 7. The coumarone resin can be replaced by polyvinyl acetate.

(Embodiment 9)

A method for using dental acrylic resins in a photopolymerization is carried out in the same manner as in Embodiment 3, except that the liquid monomer is added with a coumarone resin and an alcoholic surfactant in addition to the acryloyl morpholine. In this case, the addition amounts of the acryloyl morpholine, the coumarone resin and the alcoholic surfactant are set up in the same manner as in Embodiments 7 and 8. The coumarone resin can be replaced by polyvinyl acetate.

EXAMPLE

A stainless steel sheet having a thickness of 3 mm was provided with a taper hole (large diameter: 5 mm, taper: 1/10). The stainless steel sheet was placed on a glass sheet in such a manner that the small-diameter side was positioned downwardly, and the resulting assembly was used as a hole mold. A liquid monomer of methyl methacrylate (tertiary amine content: 2.0% by weight) was added with various shrinkage controlling agents in various ratios, and the resulting liquid monomer was soaked through a brush tip, to which a polymer powder of methyl methacrylate (benzoyl peroxide content: 0.7% by weight) was then attached to mix the liquid monomer and the polymer powder at the brush tip. The sphere was filled in the taper hole of the hole mold and solidified. The molded article was once taken out of the mold and allowed to stand at room temperature for one hour to complete polymerization and curing. A flash in the large-diameter side was removed to prepare a sample. The sample was inserted in the taper hole of the stainless steel sheet from the large-diameter side and pressed at a power of 3 kgf thereby protruding a tip portion. Then, the curing shrinkage rate of the sample was calculated from a length of the protrusion.

The curing shrinkage rate (%) in the case of using acryloyl morpholine (made by KOHJIN Co., Ltd., hereinafter abbreviated as "ACMO") singly is shown in Table 1.

TABLE 1

| Sample No. | 1 | 2 | 3 | 4 | 5 | 6 |
|---|---|---|---|---|---|---|
| Addition amount of ACMO (% by weight) | 1 | 3 | 5 | 10 | 15 | 20 |
| Curing shrinkage rate (%) | 0.4 | 0.4 | 0.3 | 0.2 | 0.3 | 0.4 |

The curing shrinkage rate (%) in the case of using a coumarone resin (a trade name "Esculon", made by Nippon Steel Chemical Co., Ltd.) singly is shown in Table 2.

TABLE 2

| Sample No. | 7 | 8 | 9 | 10 | 11 | 12 |
|---|---|---|---|---|---|---|
| Addition amount of coumarone resin (% by weight) | 0.1 | 0.5 | 1.0 | 5.0 | 10 | 15 |
| Curing shrinkage rate (%) | 0.4 | 0.3 | 0.2 | 0.2 | 0.2 | 0.3 |

The curing shrinkage rate (%) in the case of using vinyl stearate (made by Shin-Etsu Vinyl Acetate Co., Ltd., hereinafter abbreviated as "STV") singly is shown in Table 3.

TABLE 3

| Sample No. | 13 | 14 | 15 | 16 | 17 | 18 |
|---|---|---|---|---|---|---|
| Addition amount of STV (% by weight) | 1 | 3 | 5 | 10 | 15 | 20 |
| Curing shrinkage rate (%) | 0.4 | 0.4 | 0.2 | 0.2 | 0.2 | 0.3 |

The curing shrinkage rate (%) in the case of using polyvinyl acetate (a trade name "AC Lac" made by The Japan Shellac Industries, Ltd., hereinafter abbreviated as "PAV") singly is shown in Table 4.

TABLE 4

| Sample No. | 19 | 20 | 21 | 22 | 23 | 24 |
|---|---|---|---|---|---|---|
| Addition amount of PAV (% by weight) | 0.1 | 0.5 | 1.0 | 5.0 | 10 | 15 |
| Curing shrinkage rate (%) | 0.4 | 0.3 | 0.2 | 0.2 | 0.2 | 0.3 |

The curing shrinkage rate (%) in the case of using isostearyl alcohol (a trade name "Fine Oxocol 180" made by Nissan Chemical Industries, Ltd., hereinafter abbreviated as "SCOL") singly is shown in Table 5.

TABLE 5

| Sample No. | 25 | 26 | 27 | 28 | 29 | 30 |
|---|---|---|---|---|---|---|
| Addition amount of SCOL (% by weight) | 0.05 | 0.1 | 0.5 | 1.0 | 5.0 | 8.0 |
| Curing shrinkage rate (%) | 0.4 | 0.3 | 0.2 | 0.2 | 0.3 | 0.4 |

The curing shrinkage rate (%) in the case of mixing two members of any one of acryloyl morpholine (ACMO), a coumarone resin (coumarone) and polyvinyl acetate (PAV) and isostearyl alcohol (SCOL) is shown in Table 6.

TABLE 6

| Sample No. | 31 | 32 | 33 | 34 | 35 | 36 | 37 | 38 | 39 |
|---|---|---|---|---|---|---|---|---|---|
| Addition amount of ACMO (% by weight) | 0.4 | 5.0 | 10.0 | — | — | — | — | — | — |
| Addition amount of coumarone (% by weight) | — | — | — | 0.4 | 4.0 | 8.0 | — | — | — |
| Addition amount of PAV (% by weight) | — | — | — | — | — | — | 0.4 | 4.0 | 8.0 |
| Addition amount of SCOL (% by weight) | 0.1 | 3.0 | 5.0 | 0.1 | 1.0 | 2.0 | 0.1 | 1.0 | 2.0 |
| Curing Shrinkage rate (%) | 0.3 | 0.2 | 0.2 | 0.3 | 0.2 | 0.3 | 0.3 | 0.2 | 0.3 |

The curing shrinkage rate (%) in the case of mixing three members of acryloyl morpholine (ACMO), a coumarone resin (coumarone) and isostearyl alcohol (SCOL) is shown in Table 7.

TABLE 7

| Sample No. | 40 | 41 | 42 | 43 | 44 | 45 | 46 | 47 | 48 |
|---|---|---|---|---|---|---|---|---|---|
| Addition amount of ACMO (% by weight) | 0.3 | 5.0 | 8.0 | 10.0 | 11.0 | 10.0 | 9.0 | 8.0 | 7.0 |
| Addition amount of coumarone (% by weight) | 0.1 | 0.5 | 1.0 | 1.0 | 1.5 | 1.5 | 2.0 | 2.0 | 3.0 |
| Addition amount of SCOL (% by weight) | 0.1 | 0.1 | 0.5 | 0.5 | 1.0 | 1.0 | 1.5 | 1.5 | 2.0 |
| Curing Shrinkage rate (%) | 0.2 | 0.2 | 0.1 | 0.1 | 0.1 | 0.1 | 0.2 | 0.2 | 0.2 |

The curing shrinkage rate (%) in the case of mixing three members of acryloyl morpholine (ACMO), polyvinyl acetate (PAV) and isostearyl alcohol (SCOL) is shown in Table 8.

TABLE 8

| Sample No. | 49 | 50 | 51 | 52 | 53 | 54 | 55 | 56 | 57 |
|---|---|---|---|---|---|---|---|---|---|
| Addition amount of ACMO (% by weight) | 0.3 | 5.0 | 8.0 | 10.0 | 11.0 | 10.0 | 9.0 | 8.0 | 7.0 |
| Addition amount of PAV (% by weight) | 0.1 | 0.5 | 1.0 | 1.0 | 1.5 | 1.5 | 2.0 | 2.0 | 3.0 |
| Addition amount of SCOL (% by weight) | 0.1 | 0.1 | 0.5 | 0.5 | 1.0 | 1.0 | 1.5 | 1.5 | 2.0 |
| Curing shrinkage rate (%) | 0.2 | 0.2 | 0.1 | 0.1 | 0.1 | 0.1 | 0.2 | 0.2 | 0.2 |

In the light of the above, according to the present invention, not only the curing shrinkage rate of the curing shrinkage generated at the time of polymerization can be readily lowered to 0.3% or less, but also the method of the invention can be applied to a denture, a denture base, a casting pattern, fillers or cements similarly to the conventional techniques.

While the invention has been described in detail and with reference to specific embodiments thereof, it will be apparent to one skilled in the art that various changes and modifications can be made therein without departing from the spirit and scope thereof.

What is claimed is:

1. In a method for using dental acrylic resins which comprises mixing a liquid monomer of methyl methacrylate with a polymer powder of methyl methacrylate, forming the mixture into an arbitrary shape by molding, filling, applying or other means, and then polymerizing and curing the formed mixture, the improvement wherein at least one compound selected from the group consisting of acryloyl morpholine, coumarone resin, vinyl stearate, and alcoholic surfactants and mixtures thereof with polyvinyl acetate is added to the liquid monomer as a shrinkage controlling agent to lower curing shrinkage caused by polymerization.

2. A method for using dental acrylic resins as claimed in claim 1, wherein said shrinkage controlling agent is a mixture of any one of acryloyl morpholine, coumarone resin or polyvinyl acetate with an alcoholic surfactant.

3. A method for using dental acrylic resins as claimed in claim 1, wherein said shrinkage controlling agent is a mixture of either coumarone resin or polyvinyl acetate with acryloyl morpholine and an alcoholic surfactant.

4. A method for using dental acrylic resins as claimed in claim 1, wherein said alcoholic surfactant is isostearyl alcohol.

5. An acrylic resin composition comprising:
(a) liquid monomeric methyl methacrylate,
(b) powdered polymeric methyl methacrylate, and (c) as a shrinkage control agent, at least one compound selected from the group consisting of acryloyl morpholine, coumarone resin, vinyl stearate, an alcoholic surfactant and mixtures of these compounds with polyvinyl acetate.

6. A composition as claimed in claim 5, wherein said shrinkage control agent is a mixture of any one of acryloyl morpholine, coumarone resin or polyvinyl acetate with an alcoholic surfactant.

7. A composition as claimed in claim 5, wherein said shrinkage control agent is a mixture of either coumarone resin or polyvinyl acetate with acryloyl morpholine and an alcoholic surfactant.

8. A composition as claimed in claim 5, wherein said alcoholic surfactant is isostearyl alcohol.

9. A composition according to claim 5, wherein the shrinkage control agent comprises acryloyl morpholine or vinyl stearate and is present in an amount of 5 to 15% based on the weight of monomeric methyl methacrylate.

10. A composition according to claim 5, wherein the shrinkage control agent comprises a polymer of coumarone, and is present in an amount of 0.5 to 10% based on the weight of monomeric methyl methacrylate.

11. A composition according to claim 5, wherein the shrinkage control agent comprises stearyl alcohol, oleyl alcohol, pentadecyl alcohol or pentaerythritol and is present in an amount of 0.1 to 5% based on the weight of monomeric methyl methacrylate.

* * * * *